(12) United States Patent
Mazanec

(10) Patent No.: US 9,782,600 B2
(45) Date of Patent: Oct. 10, 2017

(54) SELF-REGULATING TRANSCUTANEOUS ENERGY TRANSFER

(75) Inventor: Paul Richard Mazanec, Blaine, MN (US)

(73) Assignee: ENVOY MEDICAL CORPORATION, North Mankato, MN (US)

( * ) Notice: Subject to any disclaimer, the term of this patent is extended or adjusted under 35 U.S.C. 154(b) by 1366 days.

(21) Appl. No.: 12/544,367

(22) Filed: Aug. 20, 2009

(65) Prior Publication Data

US 2011/0046699 A1 Feb. 24, 2011

(51) Int. Cl.
*A61N 1/378* (2006.01)
*H02J 7/02* (2016.01)

(52) U.S. Cl.
CPC .......... *A61N 1/3787* (2013.01); *H02J 7/025* (2013.01)

(58) Field of Classification Search
CPC .............................. A61N 1/37; A61N 1/3787
USPC ................................................ 607/33, 61, 65
See application file for complete search history.

(56) References Cited

U.S. PATENT DOCUMENTS

| | | | |
|---|---|---|---|
| 4,430,610 A * | 2/1984 | Yoshida et al. | 324/510 |
| 4,812,764 A * | 3/1989 | Bendall | 324/318 |
| 5,095,224 A * | 3/1992 | Renger | 327/110 |
| 5,690,693 A * | 11/1997 | Wang et al. | 607/61 |
| 5,702,431 A | 12/1997 | Wang et al. | |
| 6,212,431 B1 * | 4/2001 | Hahn et al. | 607/61 |
| 6,442,434 B1 * | 8/2002 | Zarinetchi et al. | 607/61 |
| 7,428,438 B2 | 9/2008 | Parramon et al. | |

(Continued)

OTHER PUBLICATIONS

International Search Report from PCT application No. PCT/US2010/043002.

*Primary Examiner* — Christopher A Flory
(74) *Attorney, Agent, or Firm* — Seager, Tufte & Wickhem LLP

(57) ABSTRACT

A rechargeable battery system and method are disclosed, in which an implantable medical device (IMD) regulates its transfer of energy from a separate charger unit. For recharging, a charger unit is brought into proximity to the implanted device. An oscillating current is generated in a primary coil, located in the charger. By inductive coupling through an oscillating magnetic field, an alternating current is generated in a secondary coil, which is implanted in or near the implanted device. The alternating current then passes through a half-wave or full-wave rectifier to form a one-sided current, then passes through a regulator to form an essentially direct current, which is in turn directed to the rechargeable battery in the implanted device. The secondary coil has a controllable damped resonant frequency, which can be dynamically tuned away from the driving frequency of the primary coil by a variable resistor and/or by varying a duty cycle of a rapidly switched electrical element. If a control loop in the implant senses that more power is being received at the second coil than is actually being used to recharge the battery, the control loop temporarily changes the variable resistance. When this happens, the resonant frequency of the secondary coil is detuned slightly away from the driving frequency, so that less of the incoming power is absorbed by the secondary coil. Alternatively, the secondary coil may be temporarily short-circuited. With less or no excess power entering the circuitry of the implant, the problem of overheating is mitigated.

15 Claims, 5 Drawing Sheets

(56) References Cited

U.S. PATENT DOCUMENTS

| | | | |
|---|---|---|---|
| 7,751,902 B1* | 7/2010 | Karunasiri | 607/61 |
| 8,185,212 B2* | 5/2012 | Carbunaru et al. | 607/61 |
| 2004/0098068 A1* | 5/2004 | Carbunaru et al. | 607/60 |
| 2005/0251225 A1* | 11/2005 | Faltys et al. | 607/57 |
| 2005/0288739 A1 | 12/2005 | Hassler et al. | |
| 2007/0005141 A1 | 1/2007 | Sherman | |
| 2009/0112291 A1 | 4/2009 | Wahlstrand et al. | |

* cited by examiner

SELF-REGULATING TRANSCUTANEOUS ENERGY TRANSFER

CROSS-REFERENCE TO RELATED APPLICATIONS

Not Applicable

STATEMENT REGARDING FEDERALLY SPONSORED RESEARCH OR DEVELOPMENT

Not Applicable

BACKGROUND OF THE INVENTION

Field of the Invention

The present invention is directed to implantable medical devices, and more particularly to recharging of batteries in implantable medical devices.

Description of the Related Art

For electrical medical devices that are surgically implanted within the body of a patient, a recent improvement is the development of rechargeable batteries. Rather than undergoing surgery to remove or replace a device that has a dead battery, a patient may now undergo periodic recharging sessions, which are far less invasive and far less expensive.

For instance, a typical first-generation implantable hearing aid may last around six to nine years with its non-rechargeable battery. More recently developed hearing aids that use rechargeable batteries may last only about six to twelve weeks between recharging sessions, but the recharging sessions are simple, quick, inexpensive, non-invasive, and are completely painless. These rechargeable batteries may prolong the life of the device substantially, and the patient may be able to use the same implantable hearing aid for up to 20, 30, 40 years or more without subsequent surgery.

The use of rechargeable batteries in implantable devices required the development of a wireless power interface for recharging, using inductive coupling between two wire coils. Inductive designs have been used successfully in implantable medical devices such as defibrillators, insulin pumps, spinal cord stimulators, deep-brain stimulators and left-ventricular assist devices. Inductive designs have also been used successfully in commercial products such as cordless toothbrushes.

In an inductive design, current flowing in one coil causes a current to flow in an adjacent coil. For implantable medical devices, one coil (referred to as the "secondary" coil) is implanted under the skin of the patient, and the other coil (referred to as the "primary" coil) is in an external charger unit that is held against the skin or in close proximity of the patient during the recharging process.

The physical mechanism for energy transfer in an inductive design is similar to that used in transformers. A time-varying, typically sinusoidal, alternating current (AC) is passed through the primary coil. The time-varying current produces a time-varying magnetic field in the vicinity of the primary coil, which decreases in strength with increasing distance away from the primary coil. The time-varying magnetic field passes easily through the skin and tissue of the patient, and does not damage the skin or tissue in any way. The time-varying magnetic field causes a time-varying voltage to form in the secondary coil, and since the secondary coil is a good conductor, produces a time-varying current in the secondary coil. If the primary coil is driven at a particular frequency, such as 10 kHz, 100 kHz or 1 MHz, then the current created in the secondary coil also flows at the particular frequency, namely 10 kHz, 100 kHz or 1 MHz. The current in the secondary coil is then rectified, regulated, and directed toward recharging the battery.

A detailed example, with circuitry, is provided in the article by PENGFEI LI and RIZWAN BASHIRULLAH, "A Wireless Power Interface for Rechargeable Battery Operated Medical Implants", IEEE Transactions on Circuits and Systems—II: Express Briefs, October 2007, pp. 912-916, Vol. 54, No. 10, which is incorporated by reference in its entirety herein.

For any wireless power interface that transfers power from one coil to another, there is a sensitivity to alignment between the coils. Typically, the coils transmit power most efficiently when they are in close proximity, both laterally and longitudinally. As the lateral and/or longitudinal separations increase, the efficiency drops, meaning that a smaller fraction of power emitted from the primary coil is received by the secondary coil.

The highest efficiency, or fraction of radiated power that is received by the secondary coil, occurs for circular coils of the same size that are directly longitudinally adjacent to each other. The efficiency drops if the sizes and/or shapes are mismatched, and if the coils are separated longitudinally and laterally. In general, the primary and secondary coils are made as large as practical, and are located as close to the surface of the skin as practical. During an actual charging session, once a charger unit is placed, it typically doesn't move much, and the efficiency tends to be relatively stable over the length of the session. In practice, efficiencies of 15% to 80% are common.

For implantable medical devices, there are standards for a variety of quantities, including electric field strength, magnetic field strength, temperature, and many others. In particular, the temperature standard dictates that the temperature difference between the device and the surrounding tissue must be less than two degrees Celsius. Such a temperature requirement has direct implications for the electrical performance of the device.

While the device is charging, it is using a certain amount of power. For example, if the device charges at a voltage of 4.2 V and a current of 150 mA, the power consumed for charging is the product of the voltage and current, namely, 0.63 W. If the amount of power received by the secondary coil exceeds 0.63 W, the excess power is converted to heat at the implant. If left unchecked, such excess power can lead to overheating of the implant, which can exceed the mandated temperature standard and may even damage the tissue of the patient, which would be unacceptable.

There are known ways to compensate for this excessive received power, with two such examples being described below.

For the first example, the current in the primary coil is set at the factory so that the power received by the second coil never exceeds a particular value, even when the first and second coils are perfectly aligned.

We consider a numerical example. We assume that 0.2 W is the maximum excess power that can be safely converted into heat, and that 0.63 W is the power that goes into recharging the battery. Using these numbers, 0.83 W is the maximum amount of power that can be generated safely in the second coil. If the current in the second coil exceeds 0.83 W at any point, and the 0.63 W value remains constant, then more than 0.2 W is converted into heat, and the device is out of specification.

For the case when the primary and secondary coils are perfectly aligned, which produces the maximum current in the secondary coil for a given current in the primary coil, the primary coil current is set to produce a secondary coil power output of 0.83 W. In other words, the primary coil current is set at the worst case for thermal issues, which is the best alignment between primary and secondary coils. When the alignment between the primary and secondary coils is less than optimal, the secondary coil current is less than 0.83 W, and less than 0.2 W is converted into heat, which is within the specification.

Although this first example ensures that the amount of power converted into heat is within an acceptable range, the trade-off is that the charging time may be unacceptably increased. For instance, assume that the charging time is two hours for well-aligned coils. If the coils are misaligned for some reason during the charging session, such as due to a lateral or longitudinal displacement of the charger unit, the charging time may be unacceptably increased, such as to six or eight hours.

While this scheme may ensure that the there is no overheating of the implanted device or the surrounding tissue, the trade-off of potentially excessive recharging times is a shortcoming.

For the second example, the implanted device includes a control loop that uses an RF telemetry link to talk back to the charger unit. Based on the data received over the RF telemetry link, the charger unit adjusts the current in the primary loop so that the power received by the secondary loop is set to a predetermined value, such as 0.63 W. The currents may be adjusted based on periodic communications over the RF telemetry link, such as several times a second. In this manner, if the charger unit is initially placed away from its optimal location, the RF telemetry link increases the primary coil current so that the secondary coil current is at its desired value. Or, if the charger unit is moved during recharging and the coils become misaligned, the primary coil current may be increased accordingly so that the amount of current in the secondary coil remains roughly unchanged.

Use of the RF telemetry link ensures that there is no overheating of the implanted device or the surrounding tissue, while keeping the charging times down to reasonable values. However, the RF telemetry link itself adds additional size, complexity and cost to both the implanted device and the external charger unit, which is undesirable.

Accordingly, there exists a need for a mechanism that restricts the power received by the secondary coil, thereby preventing overheating of the implanted device and surrounding tissue, without introducing the additional hardware and expense of an RF telemetry link.

For reference, we review common electrical quantities and their respective units. Voltage, V, is in volts. Current, I, is in amperes. Charge, Q, is in coulombs, or amp-sec. Power, P, is in watts, or volt-amp. Resistance, R, is in ohms, or volts/amp. Capacitance, C, is in farads, or amp-sec/volt. Inductance, L, is in henries (plural of henry), or volt-sec/amp.

BRIEF SUMMARY OF THE INVENTION

An embodiment is an implantable device for receiving electrical power from an external charger unit, the external charger unit producing an oscillating current in a primary coil at a driving frequency, the oscillating current producing an oscillating magnetic field proximate the external charger unit, the implantable device comprising: a secondary coil for receiving the oscillating magnetic field and producing an alternating current at the driving frequency, the amplitude of the alternating current depending in part on a resonant profile of the secondary coil, on the driving frequency, on an amplitude of the oscillating current in the primary coil, and on the relative orientations of the primary and secondary coils; a rectifier for receiving the alternating current from the secondary coil and producing a single-sided current; a regulator for receiving the single-sided current from the rectifier and producing an essentially direct current; a rechargeable battery charged by the essentially direct current; and a control loop for controlling the resonant profile of the secondary coil in response to the amplitude of the alternating current in the secondary coil.

Another embodiment is a method of recharging a battery in a surgically implanted device, comprising: bringing an external charger unit into proximity with the implanted device; producing an oscillating current at a driving frequency in a primary coil within the external charger, producing an oscillating magnetic field proximate the external charger unit, extending the oscillating magnetic field into the implanted device; producing an alternating current at the driving frequency in a secondary coil electrically connected to the implanted device; and adjusting a damped resonant frequency of the secondary coil in response to an amplitude of the alternating current.

A further embodiment is an implantable device for receiving electrical power from an external charger unit, the external charger unit producing an oscillating current in a primary coil at a driving frequency, the oscillating current producing an oscillating magnetic field proximate the external charger unit, the implantable device comprising: a secondary coil for receiving the oscillating magnetic field and producing an alternating current at the driving frequency, the amplitude of the alternating current depending in part on the driving frequency, on an amplitude of the oscillating current in the primary coil, and on the relative orientations of the primary and secondary coils; a rectifier for receiving the alternating current from the secondary coil and producing a single-sided current; a regulator for receiving the single-sided current from the rectifier and producing an essentially direct current at a regulated voltage; a rechargeable battery charged by the essentially direct current; and a control loop for temporarily short-circuiting both ends of the secondary coil to ground.

DETAILED DESCRIPTION OF THE INVENTION

A rechargeable battery system and method are disclosed, in which an implantable medical device (IMD) regulates its transfer of energy from a separate charger unit. For recharging, a charger unit is brought into proximity to the implanted device. An oscillating current is generated in a primary coil, located in the charger. By inductive coupling through an oscillating magnetic field, an alternating current is generated in a secondary coil, which is implanted in or near the implanted device. The alternating current then passes through a half-wave or full-wave rectifier to form a one-sided current, then passes through a regulator to form an essentially direct current, which is in turn directed to the rechargeable battery in the implanted device.

The secondary coil has a controllable damped resonant frequency, which can be dynamically tuned away from the driving frequency of the primary coil by a variable resistor and/or by varying a duty cycle of a rapidly switched electrical element. If a control loop in the implant senses that more power is being received at the secondary coil than is actually being used to recharge the battery, the control loop temporarily changes the variable resistance. When this happens, the resonant frequency of the secondary coil is detuned slightly away from the driving frequency, so that less of the incoming power is absorbed by the secondary coil. Alternatively, the secondary coil may be temporarily short-circuited. With less or no excess power entering the circuitry of the implant, the problem of overheating is mitigated.

The preceding two paragraphs are merely a summary, and should not be construed as limiting in any way. A more thorough discussion follows.

Figure 1:
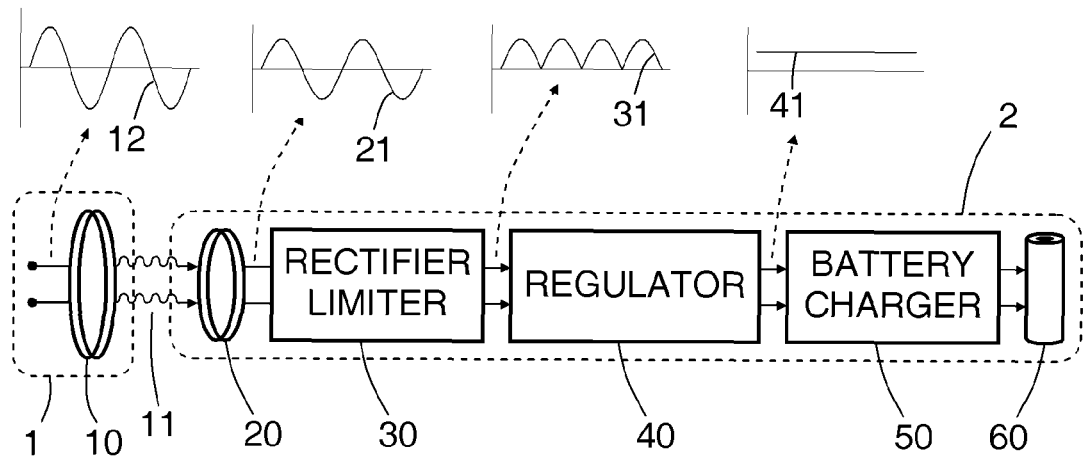
FIG. 1 is a schematic drawing of a wireless rechargeable battery system for implantable medical devices.

FIG. 1 is a schematic drawing of a wireless rechargeable battery system for implantable medical devices. Element 2 includes the elements that are implanted within the body of a patient. Note that the elements shown in FIG. 1 are only those related to the rechargeable battery of the implanted device. During recharging sessions, which may occur every few months, an external charger unit 1 is brought into proximity with the implanted device 2 for a few hours, and electrical power is transferred from the charger unit 1 to the battery 60 in the implanted device 2.

For an implantable hearing aid, which is surgically implanted in the head of the patient behind the ear, a typical charger unit 1 may be about the size of the palm of one's hand. The charger unit itself 1 is typically battery-operated and is itself rechargeable. During a typical recharging session for a hearing aid, a charger unit 1 is placed in a headband and is worn by the patient for the duration of the session, which is preferably no longer than two hours.

The charger unit 1 includes a coil 10, referred to as a "primary" coil, which is electrically driven by circuitry that produces an alternating current (AC) 12 at a particular driving frequency. A typical range of driving frequencies is from about 10 kHz to 1 MHz, and is often around 100 kHz. The driving frequency may also be outside this range. In general, it is preferable that all the chargers used with a particular implantable device all have driving frequencies that are the same or are nearly the same. In practice, there may be some spectral spreading about a central driving frequency, rather than a single driving frequency; such spreading is expected with typical electronics.

The alternating current 12 in the primary coil 10 produces an oscillating magnetic field 11 in the vicinity of the coil, which falls off in amplitude (field strength) and intensity (power) as one moves longitudinally away from the center of the coil. The magnetic field 11 oscillates at the same frequency as the driving frequency. The magnetic field 11 passes easily through the skin and through the few millimeters of tissue without causing any damage or physical changes to the skin and tissue.

The oscillating magnetic field 11 forms an inductive link between the primary coil 10 in the charger unit 1 and a secondary coil 20 in the implanted device 2. Typically, the secondary coil 20 is implanted close to the skin and lies external to a metal housing, rather than inside the metal housing. Such close placement to the skin helps reduce any losses caused by conduction of the metal housing itself.

The oscillating magnetic field 11 produces an oscillating current 21 in the secondary coil. The magnitude of the current 21 (in amperes) varies with a number of factors, but the oscillation always occurs at the driving frequency of the primary coil 10.

The oscillating current 21 is fed to a rectifier/limiter 30. The rectifier converts the oscillating current 21, which flows in both directions, to a single-ended current that flows in a single direction. The rectifier in FIG. 1 is a full-wave rectifier, which essentially "flips" the sign of every other half-cycle. Alternatively, a half-wave rectifier may be used, which essentially "zeroes out" every other half-cycle. The limiter reduces the amplitude of any peaks that lie outside a certain voltage and/or current range. Such a limiter can reduce or prevent damage to any circuitry downstream. After the rectifier/limiter 30, the current 31 is single-sided, with a series of sequential "bumps".

The single-sided current 31 is fed into a regulator 40. The regulator 40 smooths out the "bumps" by performing a time-average of the input single-sided current 31. The output from the regulator 40 is essentially the DC component of the single-sided current 31, which may be referred to as a direct current 41. Ideally, the direct current 41 has little or no component at the driving frequency, although this is not a strict requirement.

Finally, the direct current 41 feeds a battery charger 50, which directs the current to a rechargeable battery 60.

Figure 2:
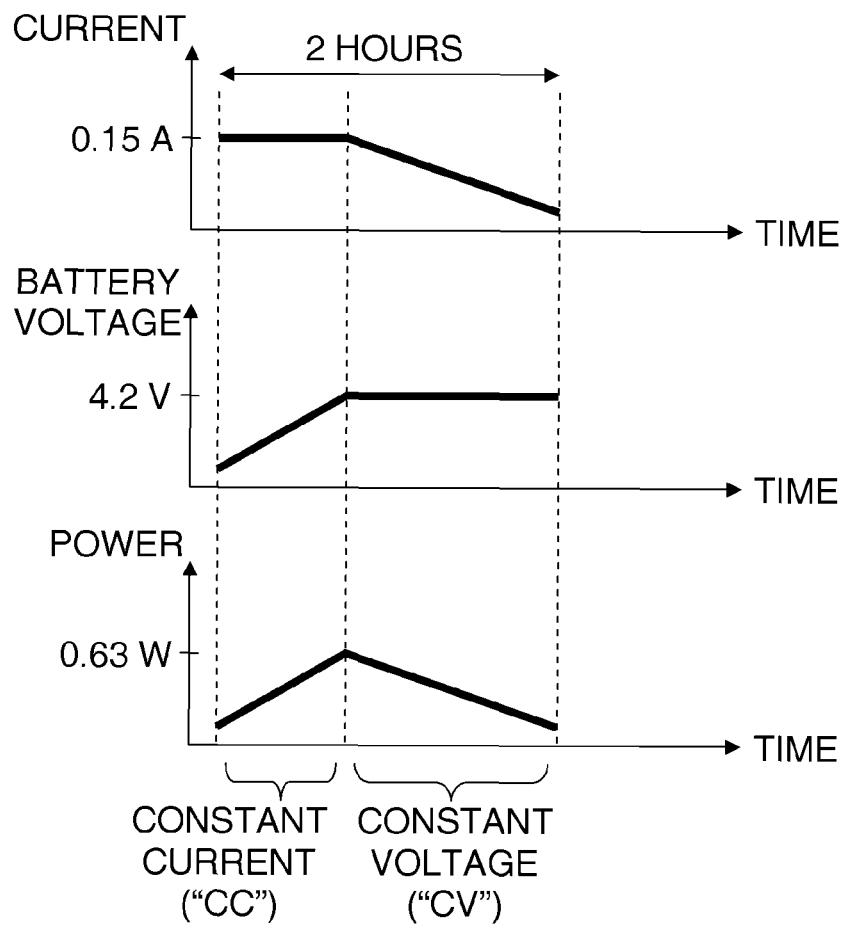
FIG. 2 is a plot of current, voltage and power for a typical recharging scheme for a rechargeable battery.

FIG. 2 is a plot of current, voltage and power for a typical recharging scheme for a rechargeable battery.

Initially, at the leftmost end of the plot, the battery is charged in "constant current" mode, in which the current remains at a constant, predetermined level, such as 0.15 A (amperes). During this time, the battery voltage slowly ramps up to a predetermined level, such as 4.2V (volts).

Physically, the constant current mode may be explained as follows. Initially, when the battery is completely drained, it takes very little "effort" to move charge into the battery. A desired amount of current can be created using a very low voltage. As the battery becomes more and more recharged, it takes increasingly more "effort" to push charge into the battery, and increasingly higher voltages are required to achieve the same current flow.

Eventually, the voltage required to produce the constant current reaches the output voltage of the battery. In the example of FIG. 2, the battery output voltage is 4.2 V. When this voltage is reached, it marks the end of the constant current portion and begins the "constant voltage" portion of recharging.

In the constant voltage portion, the voltage remains constant, typically at the output voltage of the battery, while the current that flows into the battery decreases. The current drops because it gets harder and harder to "push" charge into the battery, and since we "push" with a constant voltage, the current falls off over time.

Eventually, the current drops to a particular, predetermined level, such as 4% of the initial charge current, after which the charging is deemed as finished. Any suitable final current level may be used.

The battery capacity is measured in charge (coulombs), which represents essentially how many electrons we can move from the positive terminal to the negative terminal during recharging. Charge in coulombs is expressed equivalently in ampere-hours (A-h), with one coulomb equaling $\frac{1}{3600}$ A-h.

In general, it is desirable to complete the charging session in about two hours. In principle, the charging times may last longer, but this is less convenient for the patient, who has to remain generally stationary during the charging process. Other charging times may also be used.

It is common to run the constant current portion at a current equal to the battery capacity, divided by a charging time of two hours. For instance, for a battery capacity of 0.3 A-h, the current is run at (0.3 A-h/2 h), or 0.15 A. Other suitable currents may also be used.

The amount of power used to charge the battery may be calculated easily from the current and voltage plots in FIG. 2. The power (watts, W) is the voltage (volts, V) times the current (amperes, A). We see the power rising from essentially zero at the beginning of the constant current portion, to a peak of 0.15 A times 4.2 V, or 0.63 W, at the end of the constant current portion and the beginning of the constant voltage portion, back down to essentially zero at the end of the constant voltage portion. Note that FIG. 2 assumes that the battery voltage would be allowed to drop to zero during use in the patient. In practice, this can damage the battery and is typically not allowed. The system typically limits the battery voltage from dropping below a predetermined voltage, typically in the range of 2.8 V to 3.2 V.

We see from FIG. 2 that the power that actually gets used to charge the battery changes over the course of a charging cycle. This has thermal implications for the device, because any power that enters the device through the secondary coil either goes into charging the battery, or goes into heating the device and/or the surrounding tissue. For medical devices, there are regulations concerning heating of the surrounding tissue, so in general it is preferable to explicitly address this issue during the design phase of the device, rather than ignore it.

One known approach is to (1) determine the power value in the secondary coil that produces the maximum allowable temperature rise, when the power that goes into recharging the battery is at its lowest point or at zero, and (2) set the power level of the primary coil such that this power value at the secondary coil is never exceeded. This approach may satisfy the temperature requirement, but it may also lead to unacceptably long charging times for the device. This is not a desirable approach.

Figure 3:
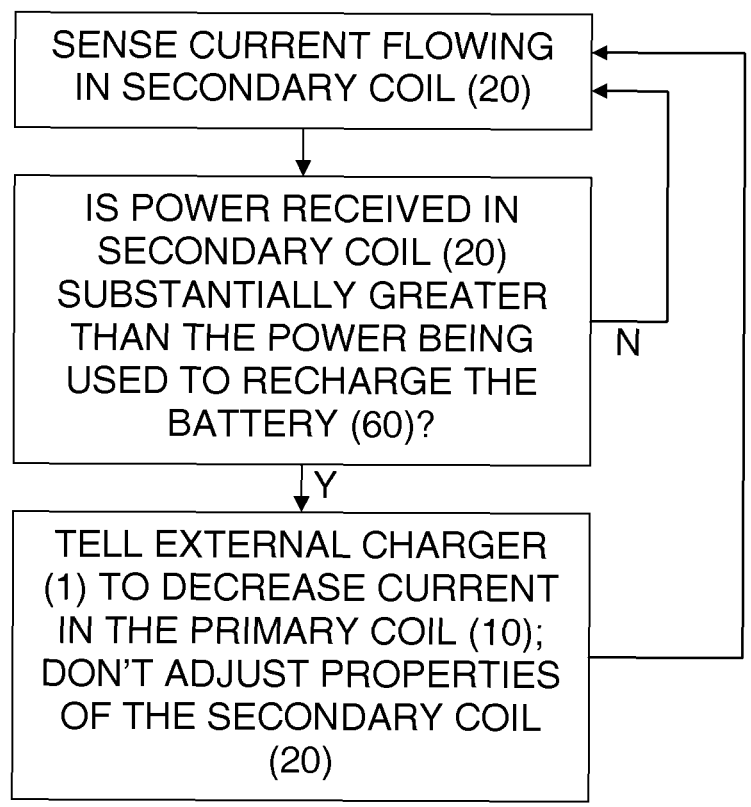
FIG. 3 is a flowchart of a known approach for dealing with thermal issues from the secondary coil.

A second known approach is shown schematically in the flowchart of FIG. 3. This approach requires communication between the implanted device and the external charger unit, such as through an RF telemetry link. In this approach, (1) the implant senses the current, or equivalently, the power, flowing in the secondary coil (2) the implant compares the sensed power with the amount of power that is actually going into charging the battery, and (3) if the power being received by the secondary coil exceeds the recharging power by a particular threshold (a fixed amount and/or a percentage) then (4) the implant communicates with the charger unit and tells it to decrease the current in the primary coil. While this approach successfully limits the excess current in the secondary coil, it also requires additional hardware and additional send/receive capabilities in both the implant and the charger unit. This leads to higher cost and higher complexity devices, which is also undesirable.

Figure 4:
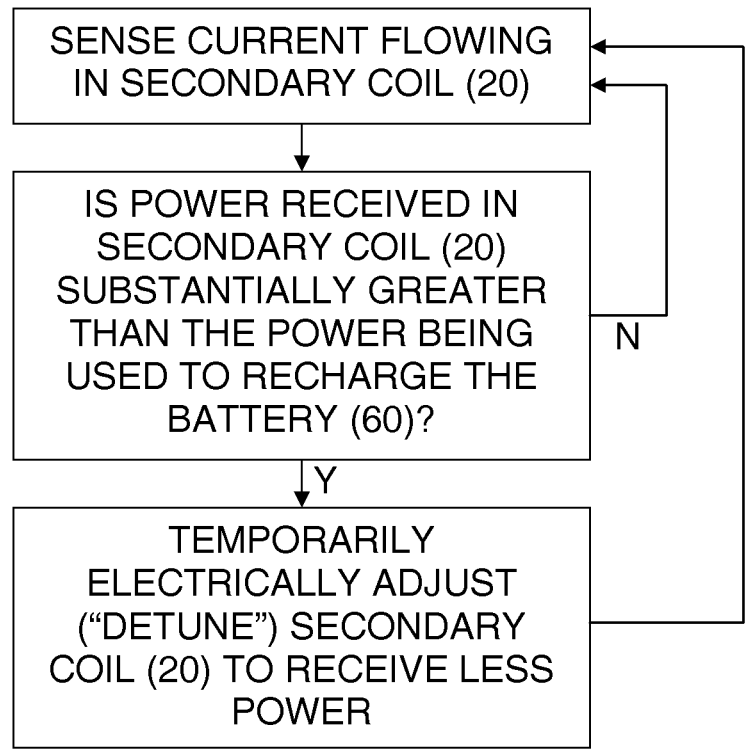
FIG. 4 is a flowchart of an exemplary present approach for dealing with thermal issues from the secondary coil.

A better approach for dealing with the thermal issues, which has short charging times and requires no additional hardware in the implant or in the charger unit, is shown in the flowchart of FIG. 4.

Here, rather than issuing a command to the charger unit 1 to turn down the current, the implant 2 electrically adjusts the secondary coil 20 to receive less power. In some cases, the secondary coil 20 is "detuned" away from the driving frequency of the primary coil 10. When detuned, the secondary coil produces a smaller current 21 for a given magnetic field 11, compared to an un-detuned secondary coil. That way, the charger unit may send out the same magnetic field strength, but because the secondary coil admits only the right amount of power to charge the battery, there is no excess power in the secondary coil. As a consequence, there are no thermal issues that arise from excess power in the secondary coil.

Figure 5:
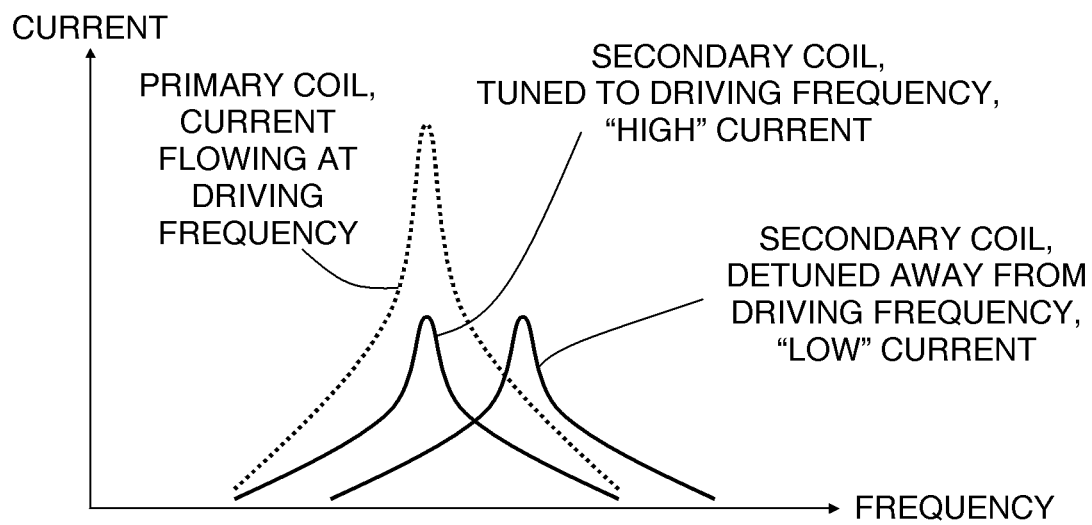
FIG. 5 is a plot of primary and secondary coil currents versus frequency.

FIG. 5 is a plot of primary and secondary coil currents versus frequency. The primary coil, shown as a dotted curve, has alternating current flowing at a driving frequency. As noted above, the peak may not be infinitely sharp, but may have a small spectral width. The secondary coil, shown as solid curves, has resonances that may be tuned to match the primary coil driving frequency (leftmost solid curve) or may be deliberately detuned away from the primary coil driving frequency (rightmost solid curve). Likewise, these secondary peaks may not be infinitely sharp, but may have small spectral widths.

The resonances of the secondary coil may be thought of in terms of a simple playground swing. When one pushes the swing at its resonant frequency, with a push that starts at the upper edge of its motion, it is very easy to impart energy to the swing, and one may easily push the swing to great heights. However, when one tries to push the swing at the wrong times, corresponding to frequencies away from the resonant frequency, one finds it quite difficult to get the swing to rise to any appreciable height, and one most likely gets knocked over in the process.

The secondary coil has a resonant frequency much like that of the playground swing. If the resonant frequency matches that of the driving frequency, it is very easy to couple energy into the secondary coil. If, however, the resonant frequency is detuned away from the driving frequency, little energy gets into the secondary coil.

Therefore, for the leftmost solid curve in FIG. 5, when the secondary coil is tuned to the driving frequency, energy easily coupled into the secondary coil, and we see a relatively "high" current in the secondary coil. Likewise, the rightmost solid curve in FIG. 5, when the secondary coil is detuned away from the driving frequency, little energy couples into the secondary coil, and we see a relatively "low" current in the secondary coil.

Figure 6:
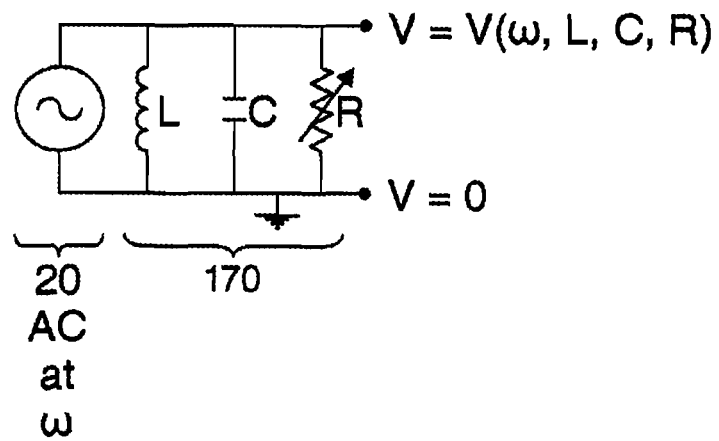
FIG. 6 is a schematic drawing of a circuit having a variable resistor.

FIG. 6 is a schematic drawing of a circuit having a variable resistor, which may be used to obtain the performance shown in FIG. 5.

The secondary coil 20 acts as an AC voltage source, with a frequency of $\omega$. The rectifier/limiter and regulator are represented as element 170 by a parallel combination of an inductor, a capacitor and a variable resistor. The output voltage V (in volts) from the circuit has a frequency dependence $V(\omega)$, which depends implicitly on the inductance L (in henries, or in volt-sec/amp), the capacitance C (in farads, or amp-sec/volt), and the resistance R (in ohms, or volts/amp). The resistance R is controllable by the implanted device.

For an infinitely large resistance R, the circuit of FIG. 6 has an undamped resonant frequency, $\omega_0$, given by:

$$\omega_0 = \frac{1}{\sqrt{LC}}.$$

For finite resistance values R, the circuit of FIG. 6 has a damped resonant frequency, $\omega_d$, given by:

$$\omega_d = \sqrt{\omega_0^2 - \left(\frac{1}{2RC}\right)^2},$$

where $\omega_0$ is the undamped resonant frequency, and R is a controllable parasitic resistance. In general, the circuit maybe tuned or detuned by adjusting the value of R.

The circuit of FIG. 6 also has a so-called "quality factor" Q, which is a dimensionless quantity that represents a sharpness of the resonance. An infinitely high quality factor Q is an infinitely sharp resonance, with essentially no width. Such an infinitely high Q is physically impossible with real electrical components, because there is always a parasitic resistance in any real circuit. In addition, such an infinitely high Q would be undesirable, because it would place extremely tight tolerances on the circuitry of the charger unit. As the numerical value of Q decreases, from over 1000, to 1000, to 100, to 10, to 1 and below 1, the width of the resonance increases. For very low values of Q, such as those below 10, there is a great deal of damping to the resonance, and the resonant peak is quite broad and ill-defined. More common values of Q are between about 10 and about 1000.

For the circuit of FIG. 6, the quality factor Q is given by:

$$Q = \frac{\sqrt{\frac{L}{C}}}{R},$$

where R is the parasitic resistance of the inductor and the capacitor along with the wire resistance. In this equation, R is usually quite small; note that this R is different from the R in an earlier equation. Note that the inductance L may correspond to an effective inductance of a group of components, rather than a single inductor. The group of components may be referred to as an "effective inductor". Inductances can be combined for series and parallel circuits in a known manner. Likewise, the capacitance C may correspond to an effective capacitance of a group of components, rather than a single capacitor. The group of components may be referred to as an "effective capacitor". Capacitances can be combined for series and parallel circuits in a known manner.

The approach described above and shown in FIG. 4-6 changes the resonance of the secondary coil to effectively detune it away from the driving frequency of the charger unit. The farther the detuning, the less power that enters the second coil. By adjusting the power that enters the second coil to match the power that is actually used to charge the battery, there is little or no excess power that goes into heating the implant or the surrounding tissue.

A second approach, described below and shown in FIG. 7-8, also reduces the power that enters the second coil, but does so by shorting both ends of the coil to ground (or together).

This second approach may be considered a subset of the first approach, in that the adjustable resistance R of FIG. 6 can take on either a very high (nearly infinite) or very low (nearly zero) value. Intermediate values may be achieved by rapidly switching the short into and out of the circuit, with the time-averaged resistance varying with the switching duty cycle.

Figure 7:
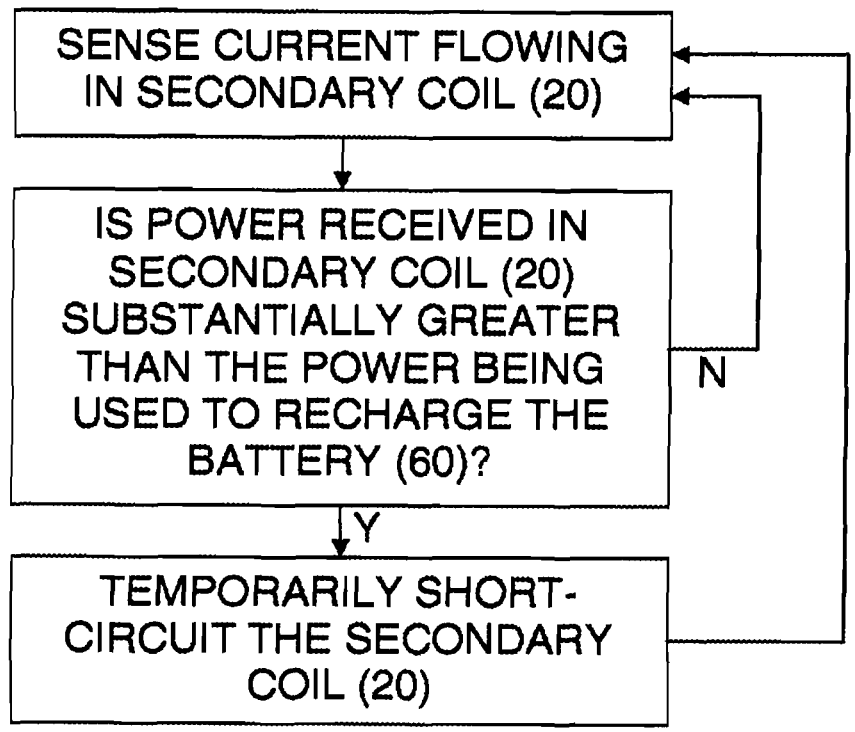
FIG. 7 is a flowchart another exemplary present approach for dealing with thermal issues from the secondary coil.

FIG. 7 is a flowchart that explicitly shows the logic of this second approach. The implanted device periodically senses the current (or, equivalently, the power or the voltage) flowing in the secondary coil 20. If the power received in the secondary coil exceeds a particular amount, then both ends of the secondary coil are temporarily shorted to ground (or together).

The threshold for determining when to short the secondary coil to ground may be determined in any number of ways. For instance, the threshold may be a fixed value that does not change over the charging cycle. Or, the threshold may be a moving value that does vary over the charging cycle. The threshold may be a fixed value above the actual power that is used to charge the battery. Or, the threshold may be a percentage above the actual recharging power. As a further alternative, it may be a combination of a fixed value with a percentage value. In general, it is desirable that any value greater than the threshold may cause undesirable heating of the implant and/or the surrounding tissue, while any value less than the threshold may not cause undesirable heating. Any or all of these may be used to define what is "substantially greater" than the power used to recharge the battery.

As an alternative to regulating strictly on the basis of excess power, it is possible to incorporate temperature measurements to help perform the regulation. For instance, temperature sensors may be placed inside the implant, on the exterior surface of the implant, and within the tissue of the patient but away from the implant. Those sensors would provide absolute temperature values, as well as temperature differences between the implant and the surrounding tissue. The values would be in essentially real time, so that they may be incorporated into the loop that controls the detuning along with, or instead of, the power values discussed above.

Figure 8:
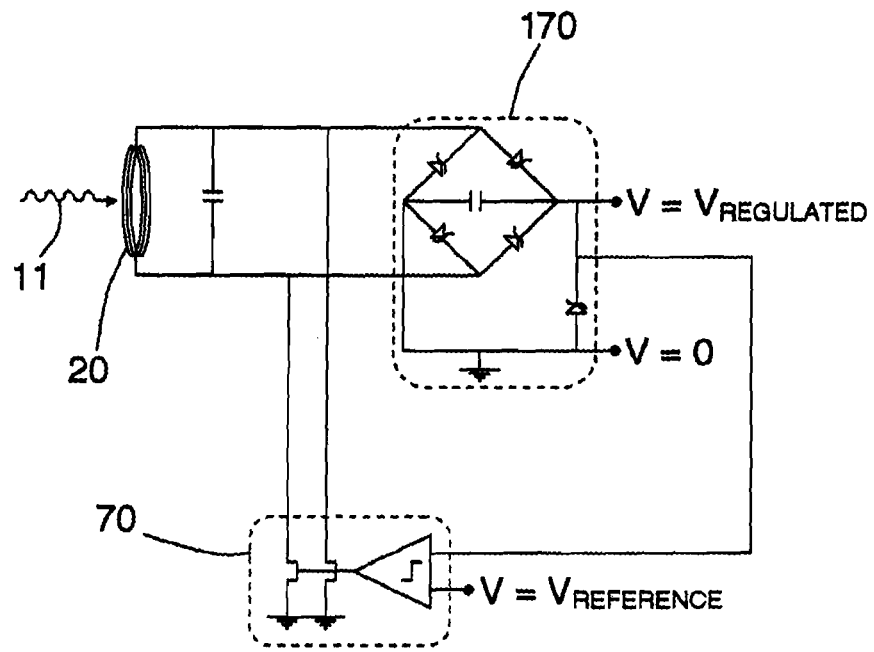
FIG. 8 is a schematic diagram of an exemplary circuit that carries out the logic of FIG. 7's flowchart.

FIG. 8 is a schematic diagram of an exemplary circuit that carries out the logic of FIG. 7's flowchart.

The charger unit (not shown) produces an oscillating magnetic field 11 that arrives at the secondary coil 20. The leads of the secondary coil 20 may have a capacitor that joins them. This capacitor is generally chosen to have a value that places the resonant frequency (defined above) at or close to the driving frequency of the primary coil, and may be referred to as a "resonant" capacitor.

The secondary coil 20 leads are directed to a rectifier/limiter and a regulator, shown together as element 170. The rectifier in this exemplary circuit is a full-wave rectifier. Alternatively, a half-wave rectifier may be used. The rectifier ensures that the current flow is one-sided, so that a DC average current is non-zero. The limiter ensures that the voltage (or current) never exceeds a particular value, which can reduce or prevent damage downstream. The capacitor in the center of the rectifier may be referred to as a "storage" capacitor, which can reduce the ripple on the output voltage by storing charge in part of each cycle and releasing it in a different part of each cycle. The limiter includes a zener diode, which serves as a voltage clamp that ensures that the output voltage V.sub.REGULATED does not exceed a particular value.

The output from the rectifier/limiter/regulator 30, 40 feeds a control loop 70. The control loop includes a comparator and two NMOS transistors that act as clamps.

If the output voltage from the regulator is greater than a reference voltage $V_{REFERENCE}$, then the output of the comparator goes high, both NMOS transistors are turned on, and both leads of the secondary coil 20 and the resonant capacitor are shorted to ground. While the coil is shorted to ground, the coil cannot receive any new power from the magnetic field. While not receiving any new power, the existing power in the circuit dissipates, the regulated voltage $V_{REGULATED}$ drops. Eventually, the regulated voltage drops below the reference voltage, the comparator output goes to low, the secondary coil leads are disconnected from ground, and the secondary coil begins to receive power again from the magnetic field.

During the time intervals that the secondary leads are shorted to ground, the implanted device is not receiving energy from the charger unit. The implant receives only the energy it needs, without any excess energy that would otherwise be dissipated as heat. In addition to eliminating any undesirable heating, the approach described above does not require communication with the charger unit, which is also beneficial.

Figure 9:
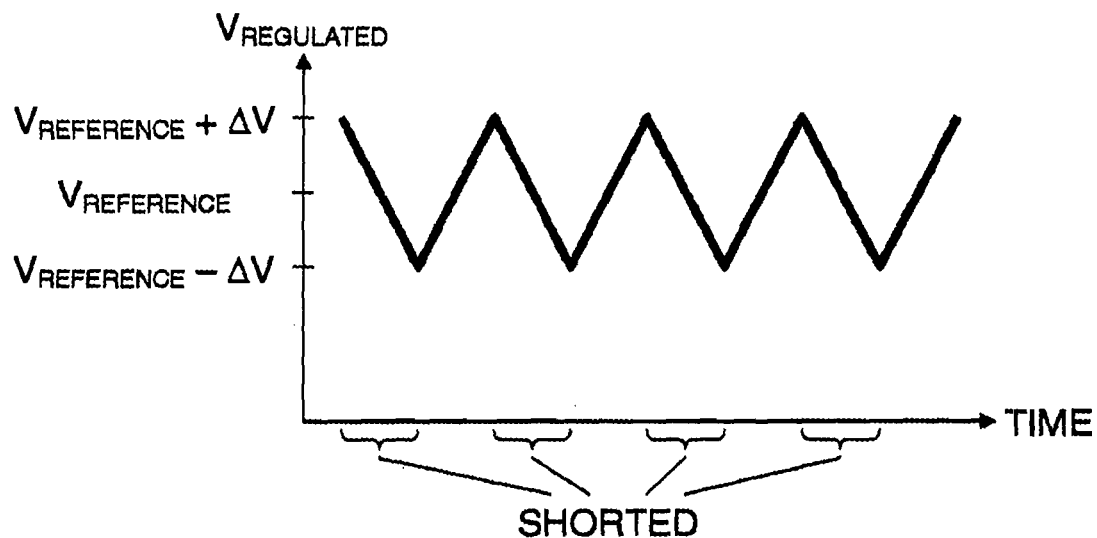
FIG. 9 is a plot of the regulated voltage versus time of the circuit in FIG. 8.

FIG. 9 is a plot of the regulated voltage versus time of the circuit in FIG. 8. Both the horizontal and vertical axes are greatly exaggerated for clarity.

The plot shows four cycles of the control loop, where the coil leads are shorted to ground for half of each cycle, and are disconnected from ground in the other half of each cycle. When the leads are shorted, the regulated voltage decays essentially linearly, with a slope proportional to the recharge current divided by the hold capacitance. Note that if the load were resistive, the voltage would decay exponentially, rather than linearly.

Averaged over a cycle, the steady-state (DC) voltage equals the reference voltage, with a variation of about $+/-\Delta V$ superimposed on the DC voltage. The variation can be controlled by adjusting the length of the intervals during which the leads are shorted. If the switching occurs very rapidly, the voltage variation $\Delta V$ will be smaller than if the switching occurs more slowly.

Although the plot in FIG. 9 has the reference voltage remaining constant over time, the reference voltage may vary over time. For instance, the reference voltage may mimic the recharging cycle of FIG. 2, by ramping up during the constant current portion, then remaining constant thereafter.

The comparator and the clamps may be used in pulse-width modulation (PWM) mode. In PWM, the switching, or connecting/disconnecting from ground, may occur more rapidly than the circuitry downstream can respond. The net effect of the PWM switching is that the switched quantity can take on any value between 0% and 100%, depending on the duty cycle of the switching. For instance, if each cycle includes 90% "on" and 10% "off", then the switched quantity may appear effectively as a DC (or slowly-varying) quantity that is 90% of the way between "off" and "on".

Here, the switched quantity may appear as a resistance, with the unswitched portion of each cycle being an effectively infinite resistance and the switched portion being a short circuit, or zero resistance. These resistance values are not truly zero and infinity, due to the finite parasitic resistance of the rest of the elements in the circuit, but the approximation is adequate for our purposes.

In this manner, the circuit of FIG. 8 can mimic that of FIG. 6, with the PWM-switched resistance between zero and infinity taking on a desired DC (or slowly-varying) value. This DC resistance value alters the resonance frequency of the secondary coil 20, as described above.

Note that the resistance may add to other resistances present in the circuitry, and may add in a known manner for series and parallel resistances.

The description of the invention and its applications as set forth herein is illustrative and is not intended to limit the scope of the invention. Variations and modifications of the embodiments disclosed herein are possible, and practical alternatives to and equivalents of the various elements of the embodiments would be understood to those of ordinary skill in the art upon study of this patent document. These and other variations and modifications of the embodiments disclosed herein may be made without departing from the scope and spirit of the invention.

I claim:

1. An implantable device for receiving electrical power from an external charger unit, the external charger unit producing an oscillating current in a primary coil at a driving frequency, the oscillating current producing an oscillating magnetic field proximate the external charger unit, the implantable device comprising:
    a secondary coil for receiving the oscillating magnetic field and producing an alternating current at the driving frequency, the amplitude of the alternating current depending in part on the driving frequency, on an amplitude of the oscillating current in the primary coil, and on the relative orientations of the primary and secondary coils;
    a rectifier for receiving the alternating current from the secondary coil and producing a single-sided current;
    a regulator for receiving the single-sided current from the rectifier and producing an essentially direct current at a regulated voltage;
    a rechargeable battery charged by the essentially direct current; and
    a control loop for temporarily short-circuiting both ends of the secondary coil to ground.

2. The implantable device of claim 1, wherein the control loop comprises a comparator for comparing the regulated voltage to a reference voltage.

3. The implantable device of claim 2,
    wherein when the regulated voltage is greater than the reference voltage, the control loop is configured to connect both ends of the secondary coil to ground; and
    wherein after the control loop connects both ends of the secondary coil to ground, the secondary coil stops receiving the oscillating magnetic field, and the regulated voltage drops.

4. The implantable device of claim 3, wherein when the regulated voltage drops below a threshold, the control loop is configured to disconnect both ends of the secondary coil from ground.

5. The implantable device of claim 3, wherein the reference voltage varies over time.

6. The implantable device of claim 5, wherein the reference voltage ramps up over a first period, then remains constant after the first period.

7. The implantable device of claim 1,
    wherein the control loop is configured to operate in pulse-width modulation to simulate a desired resistance;

wherein the desired resistance depends on a duty cycle of the pulse-width modulation; and wherein the frequency of the pulse-width modulation depends on the duty cycle.

8. A system for providing electrical power to an implantable device, comprising:

an external charger unit, the external charger unit configured to produce an oscillating magnetic field proximate the external charger unit, the oscillating magnetic field having a constant oscillating magnetic field amplitude at a driving frequency;

an implantable device including:

a secondary coil configured to receive the oscillating magnetic field and produce an alternating current at the driving frequency;

a rectifier configured to receive the alternating current from the secondary coil and produce a single-sided current;

a regulator configured to receive the single-sided current from the rectifier and produce an essentially direct current at a regulated voltage;

a rechargeable battery configured to be charged by the essentially direct current; and a control circuit configured to selectively short-circuit the secondary coil to ground.

9. The system of claim 8, wherein the control circuit comprises a comparator configured to compare the regulated voltage to a reference voltage.

10. The system of claim 9, wherein when the regulated voltage is greater than the reference voltage, the control circuit is configured to connect both ends of the secondary coil to ground.

11. The system of claim 10, wherein if the regulated voltage drops below a threshold, the control circuit is configured to disconnect both ends of the secondary coil from ground.

12. The implantable device of claim 10, wherein the reference voltage varies over time.

13. The implantable device of claim 12, wherein the reference voltage ramps up over a first period, then remains constant after the first period.

14. An implantable device for receiving electrical power from an external charger unit, the external charger unit producing an oscillating current in a primary coil at a driving frequency, the oscillating current producing an oscillating magnetic field proximate the external charger unit, the implantable device comprising:

a secondary coil for receiving the oscillating magnetic field and producing an alternating current at the driving frequency;

a rectifier for receiving the alternating current from the secondary coil and producing a single-sided current;

a regulator for receiving the single-sided current from the rectifier and producing an essentially direct current at a regulated voltage;

a rechargeable battery charged by the essentially direct current; and a control circuit configured to selectively short-circuit each end of the secondary coil to ground, the control circuit including at least two field-effect transistors, the control circuit configured such that each end of the secondary coil is switchable to ground via a corresponding one of the two field-effect transistors.

15. The implantable device of claim 14, wherein the at least two field-effect transistors are n-type MOSFETs.

* * * * *